(12) United States Patent
Van Immerseel et al.

(10) Patent No.: US 9,877,945 B2
(45) Date of Patent: Jan. 30, 2018

(54) COMPOSITION PREVENTING NECROTIC ENTERITIS IN GALLOANSERANS

(71) Applicant: PERSTORP AB, Perstorp (SE)

(72) Inventors: Filip Van Immerseel, Eke (BE); Richard Sygall, Riethoven (NL); Karolien Van Driessche, Zele (BE); Richard Ducatelle, Wortegem-Petegem (BE); Conrad Gerard Schwarzer, Beringen (BE)

(73) Assignee: PERSTORP AB, Perstorp (SE)

( * ) Notice: Subject to any disclaimer, the term of this patent is extended or adjusted under 35 U.S.C. 154(b) by 0 days.

(21) Appl. No.: 15/281,523

(22) Filed: Sep. 30, 2016

(65) Prior Publication Data

US 2017/0087115 A1    Mar. 30, 2017

Related U.S. Application Data

(62) Division of application No. 15/029,230, filed as application No. PCT/SE2014/000123 on Oct. 6, 2014, now abandoned.

(30) Foreign Application Priority Data

Oct. 14, 2013 (SE) ...................... 1300646

(51) Int. Cl.
| | |
|---|---|
| *A61K 31/22* | (2006.01) |
| *A23K 50/75* | (2016.01) |
| *A23K 20/158* | (2016.01) |
| *A23K 50/70* | (2016.01) |

(Continued)

(52) U.S. Cl.
CPC ............ *A61K 31/22* (2013.01); *A23K 20/158* (2016.05); *A23K 50/70* (2016.05); *A23K 50/75* (2016.05); *A61K 9/0056* (2013.01); *A61K 9/167* (2013.01)

(58) Field of Classification Search
CPC ...... A61K 9/0056; A61K 9/50; A61K 31/225; A61K 31/22; A23K 50/75
See application file for complete search history.

(56) References Cited

U.S. PATENT DOCUMENTS

| | | | |
|---|---|---|---|
| 6,217,915 | B1 | 4/2001 | Luchansky et al. |
| 2011/0052675 | A1 | 3/2011 | Sheu |

FOREIGN PATENT DOCUMENTS

| | | |
|---|---|---|
| CN | 102187945 A | 9/2011 |
| EP | 1224870 A1 | 7/2002 |
| EP | 2294924 A1 | 3/2011 |

(Continued)

OTHER PUBLICATIONS

Machine Translation of EP 1224970, 2002.
(Continued)

*Primary Examiner* — Jianfeng Song
(74) *Attorney, Agent, or Firm* — Polsinelli PC

(57) ABSTRACT

The present invention refers to the use of a glycerol ester composition of at least one short chain fatty acid for preventing and/or alleviating necrotic enteritis in the gastric tract of galloanserans. The glycerol ester composition comprises at least 75% by weight of glyceryl tributyrate, below 25% by weight of glyceryl dibutyrate and below 8% by weight of glyceryl monobutyrate. The present invention also refers to the use of the glycerol ester composition for modulating the gut flora of galloanserans.

22 Claims, 1 Drawing Sheet

Percentage of positive chickens (with macroscopic lesion score ≥2).

(51) Int. Cl.
    *A61K 9/16*    (2006.01)
    *A61K 9/00*    (2006.01)

(56)            References Cited

FOREIGN PATENT DOCUMENTS

| EP | 2666364 | * | 11/2013 |
|---|---|---|---|
| FR | 1600887 A | | 7/2002 |
| WO | WO-9625380 A1 | | 8/1996 |
| WO | WO-2006085346 A1 | | 8/2006 |
| WO | WO-2006115412 A2 | | 11/2006 |
| WO | WO-2012098282 | * | 7/2012 |
| WO | WO-2012140504 A1 | | 10/2012 |

OTHER PUBLICATIONS

Evonik, "Pharma Silica Insights", 2012.
International Search Report, PCT/SE2014/000123.
Stanley, D. et al "Changes in the caecal microflora of chickens following Clostridium perfringens challenge to induce necrotic enteritis". Veterinary Microbilogy. 2012, vol. 1.

* cited by examiner

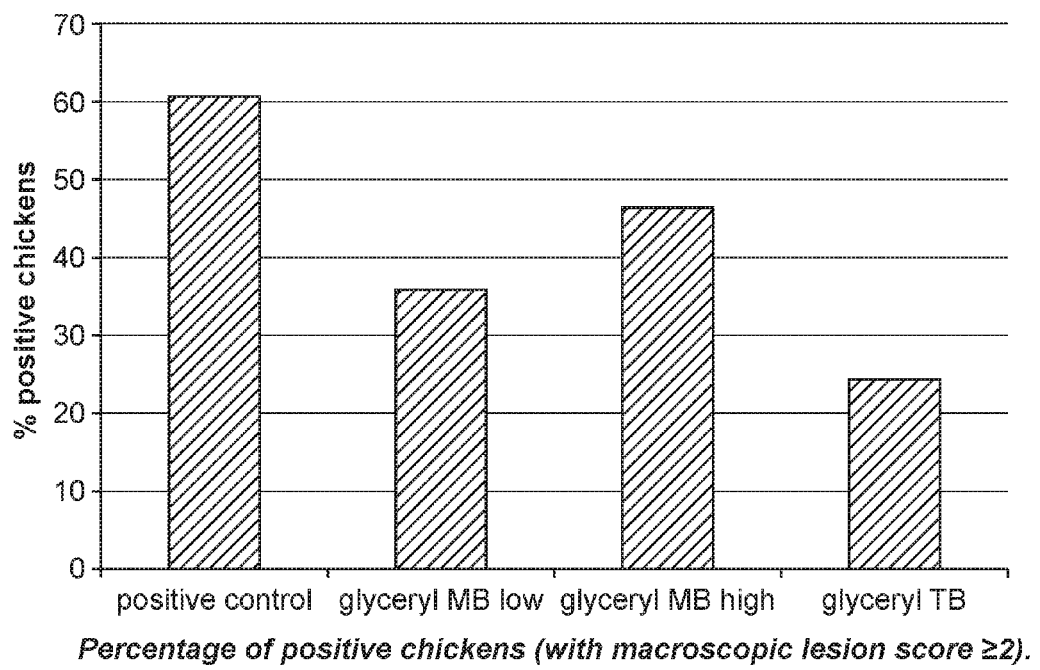
*Percentage of positive chickens (with macroscopic lesion score ≥2).*

COMPOSITION PREVENTING NECROTIC ENTERITIS IN GALLOANSERANS

FIELD OF THE INVENTION

The present invention refers to the use of a glycerol ester composition of at least one short chain fatty acid for preventing and/or alleviating necrotic enteritis in the gastric tract of galloanserans. The glycerol ester composition comprises at least 75% by weight of glyceryl tributyrate, below 25% by weight of glyceryl dibutyrate and below 8% by weight of glyceryl monobutyrate. The present invention also refers to the use of said composition for modulating the gut flora of galloanserans.

BACKGROUND OF THE INVENTION

Necrotic enteritis is an acute infection affecting galloanserans. Galloanserans are divided into the subgroups galliformes (landfowls) like chicken, turkey, grouse and pheasant, and anseriforms (waterfowls) like ducks, goose and swan. Necrotic enteritis has become an emerging problem especially among poultry and is characterized by severe necroses of intestinal mucosa. The clinical illness is usually very short and often the only signs are a sudden increase in mortality. However, birds with depression, ruffled feathers, and diarrhea may also be seen. The gross lesions are primarily found in the small intestine (jejunum), which may be ballooned, friable, and contain a foul-smelling, brown fluid.

The causative agent is the gram-positive, obligate, anaerobic bacteria *Clostridium perfringens*. There are two primary *C. perfringens* types, A and C, associated with necrotic enteritis in galloanserans. Toxins produced by the bacteria cause damage to the small intestine, but also liver lesions, and mortality.

*C. perfringens* is a nearly ubiquitous bacteria readily found in soil, dust, feces, feed, and used poultry litter. It is also a normal inhabitant of the intestines of healthy galloanserans.

Development of necrotic enteritis depends on the presence of predisposing factors, such as mucosal damage caused by coccidial pathogens and feed containing high protein levels.

Because *C. perfringens* is nearly ubiquitous, it is important to prevent coccidiosis, as well as changes in the intestinal microflora that would promote its growth. This has earlier been accomplished by routinely adding antibiotics to the feed. However, since the ban of growth promoting antibiotics in the European Union in 2006, necrotic enteritis has become an emerging disease among, for instance, poultry. There is a great need for alternative methods to counteract this disease or malfunction.

An alternative to counteracting harmful bacteria like *C. perfringens* through antibiotics is to try to balance or normalize the gut flora. The gut flora consists of a complex of microorganism species that live in the digestive tract. In this context gut is synonymous with intestinal and flora with microbiota and microflora. The microorganisms perform a host of useful functions, such as fermenting unused energy substrates, training the immune system, preventing growth of harmful, pathogenic bacteria, regulating the development of the gut, producing vitamins for the host and producing hormones to direct the host to store fats. However, in certain conditions, some species are thought to be capable of causing diseases or malfunction by producing infection or increasing cancer risk for the host.

The present invention discloses the use of a glycerol ester composition for preventing and/or alleviating necrotic enteritis in the gastric tract of galloanserans, like chicken and turkey. The use of said composition for modulating the gut flora of galloanserans is also disclosed. Use of the composition according to the invention balances or normalizes the gut flora of galloanserans in such a way that the growth of pathogenic species is inhibited and diseases like necrotic enteritis are prevented. One mechanism behind this effect is presently believed to be that the growth of helpful bacteria is favored and that this prevents the growth of pathogenic species by competing for nutrition and attachment sites to the epithelium of the colon.

The positive effects of butyric acid on gut health in poultry and other animals have been known for a long time. Different distribution forms of butyric acid have also been explored, among them distributing butyric acid in the form of glycerol esters. In recent years, a lot of interest has been directed to the use of glyceryl monobutyrate as a feed-additive to promote animal gut health.

Use of a glycerol ester composition, comprising mainly glyceryl tributyrate, has now surprisingly been found to be a more efficient way of preventing necrotic enteritis in galloanserans, such as broiler chicken, compared to giving the animal butyric acid in the form of glyceryl monobutyrate.

DETAILED DESCRIPTION OF THE INVENTION

The present invention refers to the use of a glycerol ester composition comprising a short chain fatty acid, which has proven to be an efficient way of preventing necrotic enteritis in galloanserans, such as broiler chicken. The glycerol ester composition comprises at least 75% by weight of glyceryl tributyrate, below 25% by weight of glyceryl dibutyrate and below 8% by weight of glyceryl monobutyrate. Butyric acid is known to have a positive effect on gut health in galloanserans. The present invention shows that distributing the butyric acid mainly as glyceryl tributyrate is an efficient way of preventing necrotic enteritis in galloanserans, such as broiler chicken, and it has proven to be more efficient than distributing butyric acid mainly in the form of glyceryl monobutyrate.

According to one embodiment of the present invention the glycerol ester composition comprises at least 80% by weight of glyceryl tributyrate, below 20% by weight of glyceryl dibutyrate and below 5% by weight of glyceryl monobutyrate.

According to a preferred embodiment of the present invention the glycerol ester composition comprises at least 85% by weight of glyceryl tributyrate, below 15% by weight of glyceryl dibutyrate and below 4% by weight of glyceryl monobutyrate.

According to a more preferred embodiment of the present invention the glycerol ester composition comprises at least 90% by weight of glyceryl tributyrate, below 10% by weight of glyceryl dibutyrate and below 2.5% by weight of glyceryl monobutyrate.

Free butyric acid has a very unpleasant smell, which causes handling problems. These problems can be avoided by distributing the butyric acid in the form of glycerol esters. According to one embodiment of the present invention, the amount of free butyric acid in the glycerol ester composition is below 1%, preferably below 0.5% and most preferably below 0.2% by weight. Keeping down the amount of free butyric acid also ensures that the pH in the glycerol ester composition is kept at a level where the glycerol ester will not undergo hydrolyzation into glycerol and free acid, hence, the product is kept stable.

According to one embodiment of the present invention the glycerol ester composition is adsorbed on an inert carrier, such as a silica carrier. This allows the composition to be distributed as a dry product. Such a silica carrier preferably comprises porous silica particles with an average particle size of 20-70 μm. According to one embodiment of the present invention, the glycerol ester composition is adsorbed on silica particles in a weight ratio of 50-80% glycerol ester and 20-50% silica particles.

The glycerol ester composition according to the present invention can be added to any commercially available feedstuffs for galloansers. The glycerol ester composition may be incorporated directly into commercially available feeds or fed supplementary to commercially available feeds.

According to one embodiment of the present invention the amount of glycerol ester composition fed to the galloanserans is from 0.05 to 1.5% by weight, preferably from 0.1 to 1.0% by weight of the galloanserans daily feed ration.

According to another embodiment of the present invention the amount of said glycerol ester composition is administered over time intervals of 5-10 days and is decreased over a 1-5 week period.

According to yet another embodiment of the present invention the decrease of said amount is 20-50% of the amount given during the previous interval.

BRIEF DESCRIPTION OF DRAWINGS

FIG. 1 is a graphic representation of positive chickens (with macroscopic lesion score ≥2) comparing glyceryl MB low; glyceryl MB high and glyceryl TB to a Control.

EMBODIMENT EXAMPLE

In vivo trial on the efficacy of glyceryl butyrates to control Clostridium perfringens-induced necrotic enteritis in broiler chicken.

Bacterial Strains and Vaccines

The challenge strain used in the in vivo trials, C. perfringens strain 56, was isolated from the gut of a broiler chicken with necrotic lesions from a flock with weight gain problems and has been shown to be highly virulent in earlier in vivo trials. The strain was classified as a type A strain (netB positive, beta-2 and enterotoxin negative) and produces moderate amounts of alpha toxin in vitro (Gholamiandehkordi et al., 2006).

For inoculation, the strain was grown for 24 h in Brain Heart Infusion broth (BHI, Oxoid, Basingstoke, England).

A ten-fold dose of the anticoccidial vaccine Paracox®-8 (Schering-Plough Animal Health, Brussels, Belgium), containing live, attenuated oocysts of Eimeria (E.) acervulina (two lines), E. brunetti, B. maxima, E. necatrix, E. praecox, E. mitis and E. tenella was used in this study. Nobilis Gumboro D 78 vaccine (Schering-Plough Animal Health, Brussels, Belgium) was given in the drinking water.

Animals and Housing

In this experiment, 114 broilers of mixed sex were used. They were obtained at 1 day old from a commercial hatchery. Before the trial, all rooms were decontaminated with Metatectyl® (Clim'oMedic) and with a commercial anticoccidial disinfectant (Bi-OO-Cyst®; Biolink Ltd, York, UK). The birds were divided in 4 cages of 1.5 m², on wood shavings. They were given drinking water and feed ad libitum. A 23 h/1 h light darkness program was applied.

Experimental Study Design:

The first 7 days, the chickens were fed a starter diet and from day 8 until 15, a grower diet. Both the starter and the grower diet were a wheat/rye (43%/7.5%) based diet, with soybean meal as protein source. From day 17 onwards, the same diet was used with the exception that fishmeal (30%) was used as a protein source. The feed was provided by the Institute for Agricultural and Fisheries Research (ILVO). The tested products were mixed in the feed. The Gumboro vaccine was given in the drinking water at day 16 in all groups. All groups were challenged orally one time a day with approximately $4.10^8$ cfu C. perfringens strain 56 at days 17, 18, 19 and 20. At day 18 all birds were orally inoculated with a ten-fold dose of Paracox-8™. At days 21, 22 and 23, 9 animals of each group were euthanized by intravenous sodium pentobarbital injection.

Model:

TABLE 1

Time schedule for the in vivo study

|  | d16 | d17 | d18 | d19 | d20 | d21 | d22 | d23 |
|---|---|---|---|---|---|---|---|---|
| Gumboro | x | | | | | | | |
| Feed + fishmeal | | x | x | x | x | x | x | x |
| Inoculation C. perfringens | | x | x | x | x | | | |
| Paracox ® × 10 | | | x | | | | | |
| Scoring | | | | | | x | x | x |

Products Tested:

Pen 1: positive control

Pen 2: glyceryl monobutyrate (adsorbed on a silica carrier), added to the feed at a lower concentration Pen 3: glyceryl monobutyrate (adsorbed on a silica carrier), added to the feed at a higher concentration Pen 4: glyceryl tributyrate (adsorbed on a silica carrier)

The products were added to the feed at the concentrations shown in Table 2 below:

TABLE 2

Concentrations of products added to the feed (kg/ton)

| | Glyceryl monobutyrate, on silica carrier low conc | Glyceryl monobutyrate, on silica carrier high conc | Glyceryl tributyrate, on silica carrier |
|---|---|---|---|
| Week 1 | 5 | 7.5 | 5 |
| Week 2 | 2.5 | 6 | 2.5 |
| Week 3 | 2 | 5.5 | 2 |

Intestinal lesions in the small intestine (duodenum to ileum) were scored blinded as follows;

0: no gross lesions

1: congested intestinal mucosa

2: small focal necrosis or ulceration (1-5 foci)

3: focal necrosis or ulceration (5-16 foci)

4: focal necrosis or ulceration (16 or more foci)

5: patches of necrosis 2-3 cm long

6: diffuse necrosis typical of field cases

Lesion scores of 2 or more were classified as necrotic enteritis positive

Statistical Analysis

The GraphPad Prism Software, Inc was used to determine whether there were significant differences between groups. Statistical significance was determined at a P value of <0.05.

Clinical Observations

No abnormal clinical observations were observed.

3 chickens died during the trial.

1 chicken died in pen 1

2 chickens died in pen 3

Table 3 shows the number of birds with necrotic enteritis lesions for each group, at day 21, day 22 and day 23. Also, the total number of birds with lesions per group is shown.

TABLE 3

Number of birds with macroscopic necrotic enteritis lesions on the three sampling days.

| | pos control | glyceryl monobutyrate, low | glyceryl monobutyrate, high | glyceryl tributyrate |
|---|---|---|---|---|
| day 21 | 9/9 | 5/9 | 4/9 | 3/9 |
| day 22 | 4/9 | 3/9 | 5/9 | 2/9 |
| day 23 | 4/10 | 2/10 | 3/8 | 2/11 |
| total | 17/28 | 10/28 | 12/26 | 7/29 |
| Total (%) | 61 | 36 | 46 | 24 |

The percentage of positive chickens (with macroscopic lesion score=2) is shown in FIG. 1.

The results in FIG. 1 states that adding glyceryl tributyrate to the feed gives a significantly better result, with respect to preventing *Clostridium perfringens*-induced necrotic enteritis in broiler chicken, than adding glyceryl monobutyrate at either one of the two concentrations tested.

If the addition of glyceryl monobutyrate at the higher concentration is compared to the addition of glyceryl tributyrate, it is about the same weight of butyric acid that is added (making the assumption that glycerol and butyric acid have about the same molar weights). Despite this fact, glyceryl tributyrate gives a much better result (24% positive chicken in total for glyceryl tributyrate compared to 46% positive chicken in total for glyceryl monobutyrate at the higher concentration).

It is also remarkable that adding a lower concentration of glyceryl monobutyrate gives a better result than adding a higher concentration (36% positive chicken in total for glyceryl monobutyrate at the lower concentration compared to 46% positive chicken in total for glyceryl monobutyrate at the higher concentration).

The results show that using a glycerol ester composition according to the present invention is an effective way of preventing *Clostridium perfringens*-induced necrotic enteritis in galloanserans.

The embodiment example is to be construed as illustrative and not limiting in any way. The glycerol ester composition may for example comprise a blend of glycerol esters of different short chain fatty acids, such as butyric acid, propionic acid and valeric acid. The dosage levels will then have to be calculated with respect to the total amount of glycerol esters.

It may further prove to be useful to feed the glycerol ester composition to the animal for a shorter or longer period of time and to extrapolate the dosage levels accordingly.

The invention claimed is:

1. A therapeutic method for preventing and/or alleviating necrotic enteritis in the gastric tract of galloanserans, the method comprising administering a glycerol ester composition to the galloanserans in dry form, wherein the glycerol ester composition is present on a carrier and the glycerol ester composition comprises:

glyceryl tributyrate being present in an amount of at least 75% by weight of the total glycerol ester composition but less than 100% by weight of the total glycerol ester composition, glyceryl monobutyrate being present in an amount of more than 0% and below 8% by weight of the total glycerol ester compositions, glyceryl dibutyrate being present in an amount of more than 0% and below 25% by weight of the total glycerol ester composition, and free butyric acid being present in amount of more than 0% and below 0.5% by weight of the total glycerol ester composition.

2. The method according to claim 1, wherein the necrotic enteritis is caused by *Clostridium perfringens*.

3. The method according to claim 1, wherein the galloanserans are galliformes.

4. The method according to claim 1, wherein the galloanserans are anseriforms.

5. The method according to claim 1, wherein the glycerol ester composition comprises glyceryl tributyrate being present in an amount of at least 80% by weight of the total glycerol ester composition but less than 100% of the total glycerol ester composition, glyceryl monobutyrate being present in an amount not exceeding 5% by weight of the total glycerol ester composition.

6. The method according to claim 1, wherein the glycerol ester composition comprises glyceryl tributyrate being present in an amount of at least 85% by weight of the total glycerol ester composition but less than 100% of the total glycerol ester composition, and glyceryl monobutyrate being present in an amount not exceeding 4% by weight of the total glycerol ester composition.

7. The method according to claim 1, wherein the glycerol ester composition comprises glyceryl tributyrate being present in an amount of at least 90% by weight of the total glycerol ester composition but less than 100% by weight of the total glycerol ester composition, glyceryl monobutyrate being present in an amount not exceeding 2.5% by weight of the total glycerol ester composition.

8. The method according to claim 1, wherein the amount of free butyric acid in the glycerol ester composition is below 0.2% by weight of the total glycerol ester composition.

9. The method according to claim 1, wherein the carrier comprises porous silica particles.

10. The method according to claim 9, wherein the glycerol ester composition is adsorbed on the silica particles in a weight ratio of 50-80% glycerol ester and 20-50% silica particles.

11. The method according to claim 1, wherein the glycerol ester composition is fed to the galloanserans in an amount of between 0.05 to 1.5% by weight of the galloanserans' daily feed ration.

12. The method according to claim 1, wherein the glycerol ester composition is fed to the galloanserans in an amount of between 0.1 to 1.0% by weight of the galloanserans' daily feed ration.

13. The method according to claim 11, wherein the amount of the glycerol ester composition is administered over time intervals of 5-10 days and then the amount is subsequently decreased over a 1-5 week period.

14. The method according to claim 13, wherein the decrease of the amount is 20-50% of the amount given during the previous interval.

15. The method according to claim 12, wherein the amount of the glycerol ester composition is administered over time intervals of 5-10 days and then the amount is subsequently decreased over a 1-5 week period.

16. The method according to claim 3, wherein the galloanserans are galliformes selected from the group consisting of chicken, turkey, grouse and pheasant.

17. The method according to claim 4, wherein the galloanserans are anseriformes selected from the group consisting of ducks, goose and swan.

18. A therapeutic method for preventing and/or alleviating necrotic enteritis caused by *Clostridium perfringens* in the gastric tract of galloanserans, the method comprising administering a glycerol ester composition to the galloanserans in dry form, wherein the glycerol ester composition is present on a carrier and the glycerol ester composition comprises:

glyceryl tributyrate being present in an amount of at least 75% by weight of the total glycerol ester composition, but less than 100% by weight of the total glycerol ester composition, glyceryl monobutyrate being present in an amount of more than 0% and below 8% by weight of the total glycerol ester composition, glyceryl dibutyrate, and free butyric acid being present in amount of more than 0% and below 0.5% by weight of the total glycerol ester composition.

19. The therapeutic method of claim 18, wherein the glyceryl monobutyrate is present in an amount not exceeding 2.5% by weight of the total glycerol ester composition.

20. The therapeutic method of claim 19, wherein the glycerol ester composition is distributed in a feed to the galloanserans.

21. The therapeutic method of claim 20, wherein the amount of free butyric acid in the glycerol ester composition in the feed is in the range of 0.2% to 0.5% by weight.

22. The therapeutic method of claim 9, wherein the porous silica particles have an average particle size of 20-70 nm.

* * * * *